(12) United States Patent
Huatan et al.

(10) Patent No.: US 9,675,559 B2
(45) Date of Patent: *Jun. 13, 2017

(54) TREATMENT OF ADRENAL INSUFFICIENCY

(71) Applicant: Diurnal Limited, Cardiff (GB)

(72) Inventors: Hiep Huatan, Maidstone (GB); Richard Ross, Sheffield (GB); Martin Whitaker, Nottingham (GB)

(73) Assignee: Diurnal Limited, Cardiff (GB)

( * ) Notice: Subject to any disclaimer, the term of this patent is extended or adjusted under 35 U.S.C. 154(b) by 52 days.

This patent is subject to a terminal disclaimer.

(21) Appl. No.: 14/354,651

(22) PCT Filed: Nov. 19, 2012

(86) PCT No.: PCT/GB2012/052864
§ 371 (c)(1),
(2) Date: Apr. 28, 2014

(87) PCT Pub. No.: WO2013/072707
PCT Pub. Date: May 23, 2013

(65) Prior Publication Data
US 2014/0287052 A1    Sep. 25, 2014

(30) Foreign Application Priority Data
Nov. 19, 2011 (GB) .................. 1119985.8

(51) Int. Cl.
*A61K 9/50*    (2006.01)
*A61K 31/573*    (2006.01)
(Continued)

(52) U.S. Cl.
CPC .............. *A61K 9/5078* (2013.01); *A23L 2/52* (2013.01); *A23L 33/10* (2016.08); *A61K 9/5026* (2013.01); *A61K 9/5042* (2013.01); *A61K 9/5047* (2013.01); *A61K 9/5089* (2013.01); *A61K 31/573* (2013.01); *A61K 9/0095* (2013.01)

(58) Field of Classification Search
None
See application file for complete search history.

(56) References Cited

U.S. PATENT DOCUMENTS

2005/0287211 A1    12/2005    Yoshida et al.
2007/0281007 A1    12/2007    Jacob
(Continued)

FOREIGN PATENT DOCUMENTS

EP           0 474 098 A1    3/1992
WO    WO 97/25980 A1    7/1997
(Continued)

OTHER PUBLICATIONS

Merke, Deborah P., and Stefan R. Bornstein. "Congenital adrenal hyperplasia." The Lancet (2005) 365:2125-2136.*
(Continued)

*Primary Examiner* — Bethany Barham
*Assistant Examiner* — Peter Anthopolos
(74) *Attorney, Agent, or Firm* — Klarquist Sparkman, LLP

(57) ABSTRACT

The disclosure relates to the treatment of adrenal insufficiency with particular but not limiting application to pediatric treatment regimens, the treatment of the elderly and non-human animals.

26 Claims, 1 Drawing Sheet

(51) Int. Cl.
  *A23L 2/52* (2006.01)
  *A23L 33/10* (2016.01)
  *A61K 9/00* (2006.01)

(56) References Cited

U.S. PATENT DOCUMENTS

| | | |
|---|---|---|
| 2008/0187586 A1 | 8/2008 | Skrtic et al. |
| 2009/0035375 A1 | 2/2009 | Skrtic et al. |
| 2010/0029602 A1 | 2/2010 | Arkin |
| 2016/0081942 A1 | 3/2016 | Huatan et al. |

FOREIGN PATENT DOCUMENTS

| | | |
|---|---|---|
| WO | WO 2005/102271 A2 | 11/2005 |
| WO | WO 2005/102287 A2 | 11/2005 |
| WO | WO 2010/032006 A2 | 3/2010 |
| WO | WO 2010/115615 A1 | 10/2010 |
| WO | WO 2011/144327 A1 | 11/2011 |
| WO | WO 2014/184525 A1 | 11/2014 |

OTHER PUBLICATIONS

Handbook of Pharmaceutical Excipients. Pharmaceutical Press 2005 (5th Edition) 712-714.*
Cellets®: Pellets from microcrystalline cellulose. Product Information (Aug. 2008).*
Remington: The science and practice of pharmacy. 21st Edition (2005) pp. 899-900.*
Debono and Ross, "Doses and Steroids to be Used in Primary and Central Hypoadrenalism," *Ann. d'Endocrinol.* 68:265-267, 2007.
GB Search Report for Application No. GB1119985.8, dated Mar. 1, 2012.
Johannsson et al., "Improving Glucocorticoid Replacement Therapy Using a Novel Modified-Release Hydrocortisone Tablet: A Pharmacokinetic Study," *Eur. J. Endocrinol.* 161:119-130, 2009.
Lennernas et al., "Relacement Therapy of Oral Hydrocortisone in Adrenal Insufficiency: The Influence of Gastrointestinal Factors," *Expert Opin. Drug Metab. Toxicol.* 4:749-758, 2008.
Dauber et al., "Noctural Dexamethasone versus Hydrocortisone for the Treatment of children with Congenital Adrenal Hyperplasia," *Intl. J. Pediatric Endocrinol.* 2010:347636-347643, 2010.
Möschwitzer and Müller, "Spray Coated Pellets as Carrier System for Mucoadhesive Drug Nanocrystals," *Eur. J. Pharm. Biopharm.* 62:282-287, 2006.
International Search Report and Written Opinion mailed on Jul. 24, 2014 for International Application No. PCT/GB2014/051442 (10 pages).
GB 1308933.9 Search Report under Section 17(5) issued Oct. 28, 2013 (3 pages).

* cited by examiner

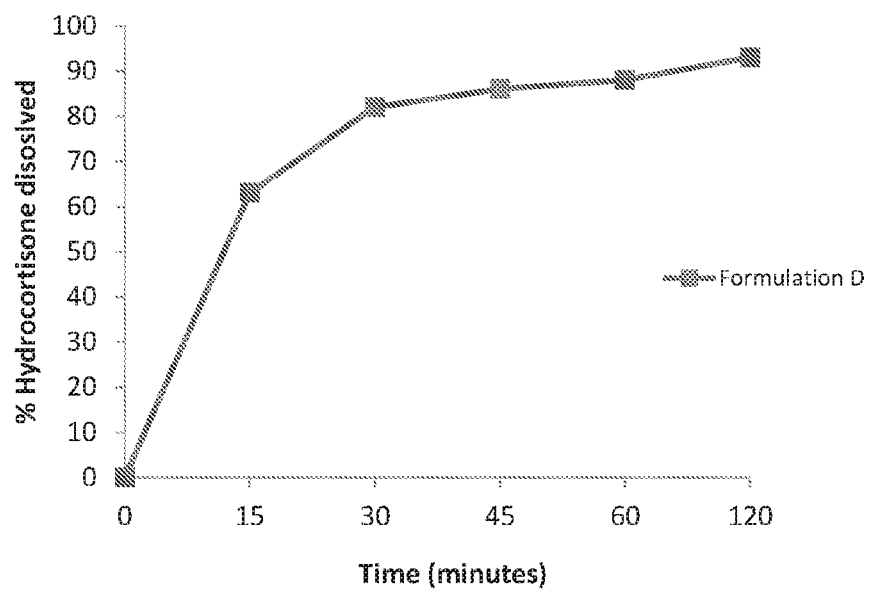

TREATMENT OF ADRENAL INSUFFICIENCY

CROSS REFERENCE TO RELATED APPLICATIONS

This is the U.S. National Stage of International Application No. PCT/GB2012/052864, filed Nov. 19, 2012, which was published in English under PCT Article 21(2), which in turn claims the benefit of Great Britain Application No. 1119985.8, filed Nov. 19, 2011.

FIELD OF THE INVENTION

The invention relates to the treatment of adrenal insufficiency with particular but not limiting application to paediatric treatment regimens, the treatment of the elderly and non-human animals.

BACKGROUND TO THE INVENTION

Adrenal failure occurs in approximately $1/10,000$ of the adult population and $1/16,000$ of infants. It may be due to either primary adrenal failure (e.g. Addison's disease commonly occurring following autoimmune damage to the adrenal gland or TB), or secondary adrenal failure (which occurs due to pituitary failure which may be caused by a pituitary tumour or surgery). In causes of primary adrenal failure ACTH levels from the pituitary will be high and in secondary adrenal failure ACTH levels are inappropriately low. Tertiary adrenal failure is another common cause of adrenal failure is suppression of the normal pituitary-adrenal axis by steroid therapy such as that used for chemotherapy, rheumatoid arthritis and asthma. A further condition that results from adrenal failure is glucocorticoid-remediable aldosteronism (GRA) which results from increased secretion of aldosterone. Thus, adrenal failure is a relatively common condition and many patients have to take long-term steroid replacement therapy.

It is apparent that dosing regimens for the treatment of children, adults and elderly adults will vary depending on a number of parameters such as developmental stage and physiological state.

For example, the treatment of children suffering adrenal insufficiency is problematic for a number of reasons and treatment regimens used to treat adult subjects suffering adrenal failure are not equivalent when applied to non-adults [e.g. neonates, infants, small child, and pre-pubescent child]. The treatment of paediatric adrenal insufficiency has particular problems and requires pharmaceutical formulations that address the pharmacokinetic and pharmacodynamic problems of dosing infants. Hepatic microsomal enzyme processes are not fully developed in infants which may require alternative dosage and administration regimens of one, two or more doses of drug. In drugs that are cleared by the liver there is a gradual increase in drug clearance rate throughout childhood to the fully mature adult which once again requires careful monitoring of dose and dosage regimen.

Current preparations of hydrocortisone cannot adequately replace cortisol deficiency especially in the paediatric population because the formulations used do not allow the flexibility of (low) dose hydrocortisone to reproduce physiological levels of cortisol. For example, after diagnosis with adrenal insufficiency, usually at birth, a common dose of hydrocortisone prescribed in the United Kingdom is 7.5 mg per day divided into three equal doses (i.e. 3×2.5 mg per day). However, the smallest hydrocortisone tablet currently available in the United Kingdom and most of Europe is 10 mg hydrocortisone (5 mg hydrocortisone—Cortef® in the US). These tablets are often halved and/or quartered or crushed and repackaged to provide the required dose. Where a 10 mg hydrocortisone tablet is available, the 2.5 mg dose is usually the smallest dose attainable because it is difficult to accurately divide a tablet into more than four quarters. Where a 5 mg hydrocortisone tablet is available, a 1.25 mg dose is usually the smallest dose attainable. In the United Kingdom, paediatric clinicians and patients believe that the 7.5 mg daily dose is far too high for neonates (0-28 days old), infants (1-24 months old) and young children (2-6 years old) and that the disease is not being adequately controlled but rather over treated. For example overtreatment with glucocorticoids such as hydrocortisone means that children suffer from very poor growth, poor weight-control and metabolic issues through development. One result of this glucocorticoid overtreatment in early childhood is that children never reached their full genetic height potential, suffer from low bone density at puberty (and into adulthood) and are at risk of obesity and a poor metabolic profile with increased cardiovascular risk factors in adult life.

For infants, crushed hydrocortisone tablets can give rise to dosing inconsistency as the poor solubility of the drug requires the use of suspension delivery methods which can lead to dose in homogeneity. Individual case reports have shown poor control of congenital adrenal hyperplasia with either excessive cortisol levels or low cortisol levels in association with poor androgen control after oral administration of crushed tablets. In addition infants and children do not like the taste of hydrocortisone making administration difficult and compliance unreliable. Studies investigating the bio-availability/pharmacokinetics on the stability of these tablets, when divided, have shown suboptimal treatment, questioning the efficacy and ethics of such practice, particularly in the most vulnerable patients of all, neonates and infants.

Common problems in delivering hydrocortisone in accordance with levels required for normal and healthy growth in children are that: (a) currently available tablet formulations do not enable accurate, low dose titration of hydrocortisone, (b) such tablet formulations when crushed to facilitate suspension delivery suffer poor dose homogeneity and have only a limited shelf-life (less than 1-month at 4 degrees Centigrade) necessitating refrigerated storage and further complicating end use. Furthermore, the elderly are presented with different problems. Geriatric patients are more susceptible to the side effects of administered drugs. The elderly may often be taking multiple medicines that may interact with one another to increase the likelihood of side effects being manifested during treatment. With aging comes a decline in organ function and consequently drugs may be metabolized less efficiently in the elderly when compared to a mature adult. In addition with aging comes memory loss and non-compliance resulting in inadequate dosing and poor disease control. Furthermore, if a subject receiving the medication is able to taste the active ingredient upon ingestion they may refuse to comply with the prescribed dosage regimen. This is particularly acute with paediatric and elderly patients who may have problems swallowing tablets or capsules. This is also a problem if multiple dosages are required throughout the day.

It is now increasingly recognised that all patients with adrenal insufficiency are receiving excess glucocorticoid because of the limited ability to dose titrate. This excess glucocorticoid is associated with an increased mortality rate in patients with adrenal insufficiency. In adults, optimal treatment requires at least thrice daily dosing with a weight related dose. Total daily doses vary between 10 and 30 mg but as a larger dose is required in the morning current dosage formulations do not allow adequate titration putting patients at risk of either over or under treatment at different times of the day.

This disclosure relates to improved pharmaceutical formulations of hydrocortisone and their use in the control of adrenal insufficiency in neonates, infants, small children, pre-pubescent children and the elderly. We also disclose regimens that show improved disease control, improved compliance and reduced side effect profile.

Statements of Invention

According to an aspect of the invention there is provided a pharmaceutical formulation adapted for oral administration comprising: a micro-particulate carrier comprising an effective amount of hydrocortisone and a binding agent and contacting said micro-particulate carrier a taste masking polymer layer wherein said composition is for use in the treatment of adrenal insufficiency in paediatric and elderly subjects.

According to an aspect of the invention there is provided a pharmaceutical composition comprising: an effective amount of hydrocortisone adapted for substantially immediate release wherein hydrocortisone is combined with at least one carrier molecule and/or polymer that confers substantially immediate dissolution of hydrocortisone when administered to a paediatric or elderly subject in need of treatment and optionally a taste masking or flavour enhancing molecule and/or polymer wherein said composition is for use in the treatment of adrenal insufficiency.

In a preferred embodiment of the invention said subject is a paediatric subject.

In an alternative preferred embodiment of the invention said subject is an elderly subject.

A paediatric subject includes neonates (0-28 days old), infants (1-24 months old), young children (2-6 years old) and prepubescent [7-14 years old]. An elderly subject includes those over about the age of 60 years old.

In a preferred embodiment of the invention an effective amount (dose) of hydrocortisone is between about 0.25 mg and 130 mg hydrocortisone per unit dosage.

Preferably said effective amount (unit dose) is about 0.25 mg, 0.5 mg, 1.0 mg, 2.0 mg, 5.0 mg, 10 mg, 20 mg and 30 mg per unit dosage.

In a preferred embodiment of the invention said carrier comprises one or more hydrophilic molecules or polymers.

In a preferred embodiment of the invention said hydrophilic molecules or polymers are selected from the group consisting of mannitol, xylitol, sucrose or glucose.

Preferably said hydrophilic molecule is in the form of a sucrose bead.

In an alternative preferred embodiment of the invention said carrier is a hydrophilic polymer.

In a preferred embodiment of the invention said hydrophilic polymer is hydroxypropylmethylcellulose or hydroxypropylethylcellulose or hydroxypropylmethyl cellulose acetylsuccinate.

In an alternative preferred embodiment of the invention said carrier is a hydrophobic polymer or small molecule.

Preferably said hydrophobic polymer is microcrystalline cellulose or dicalcium phosphate.

In a preferred embodiment of the invention said carrier comprises microcrystalline cellulose particles wherein the diameter of said particles is between 100 µm to 1200 µm.

Preferably the diameter of said particles is 100 µm to 800 µm. Preferably the diameter of the layered particles is between 400 µm to 1000 µm.

In a preferred embodiment of the invention hydrocortisone is present in or on the said carrier between the concentration 0.1-10% w/w.

More preferably the concentration of hydrocortisone in or on the said carrier is between the concentration 0.1-8% w/w.

In a preferred embodiment of the invention the binding agent is provided between 0.1%-5.0% w/w of the composition.

Preferably the binding agent is between 0.60-0.70% w/w of the composition.

In a preferred embodiment of the invention the binding agent is hydroxypropylmethyl cellulose and is provided at about 0.65% w/w.

In a preferred embodiment of the invention said composition comprises a further layer contacting said binding agent and hydrocortisone to provide a sealing layer between the binding agent and hydrocortisone and said taste masking polymer layer.

Preferably the sealing layer comprises hydroxyproplymethylcellulose.

In a preferred embodiment of the invention the sealing layer is 25-35% w/w of the composition. Preferably, the sealing layer is about 30% w/w of the composition.

Taste masking or flavour enhancement of medication is known in the art and typically involves the use of molecules/polymers to mask the taste of the active or by disguising the taste by adding the medication to a flavoured food or drink. Examples of taste masking molecules can be selected from the Handbook of Excipients [2010] which are compatible with use in the paediatric population and represents common general knowledge. Alternatively or in addition masking the taste of the active could include the use of flavoured drinks or food, for example, combining the formulation with sugar favoured drink, e.g. fruit juice, flavoured water or cordial, semi-solid foods such as sauces, e.g. apple sauce, vegetable extracts e.g. Marmite®, dairy products such as yogurts, crème fraiche, cream. When administered to neonates, infants and young children the composition is administered by opening up the capsule and adding the composition directly into an aqueous or semi-aqueous vehicle as a suspension. The composition and vehicle combination can be administered by metered spoon (disposable/re-useable), via pre-filled spoon, via syringe, via dropper, via straw, or via dose-specific method.

In a preferred embodiment of the invention said taste masking excipient is provided at between 0.5-10% w/w; preferably 0.5-5% w/w, most preferably about 2% w/w of the composition.

In a preferred embodiment of the invention said composition consists essentially of 80-90% w/w hydrocortisone, 9-16% w/w cellulose acetate and 1-4% w/w polyvinyl pyrrolidone.

In a preferred embodiment of the invention said composition consists of 80% w/w hydrocortisone, 16% w/w cellulose acetate and 4% w/w polyvinyl pyrrolidone.

In an alternative preferred embodiment of the invention said composition consists essentially of 60-80% w/w hydrocortisone, 5-10% w/w aminoalkyl methacrylate and 10-35% w/w polyvinyl acetate.

In a preferred embodiment of the invention said composition consists of 80% w/w hydrocortisone, 10% w/w aminoalkyl methacrylate and 10% w/w polyvinyl acetate.

In a preferred embodiment of the invention said composition consists of 60% w/w hydrocortisone, 10% w/w aminoalkyl methacrylate and 30% w/w polyvinyl acetate.

In a preferred embodiment of the invention said composition consists of 60% w/w hydrocortisone, 5% w/w aminoalkyl methacrylate and 35% w/w polyvinyl acetate.

In a preferred embodiment of the invention the taste masking polymer layer is a combination of hydroxyproplymethylcellulose and ethylcellulose.

In a preferred embodiment of the invention the taste masking polymer layer is provided between 1.5% w/w to 2.5% w/w of the composition. Preferably, the taste masking polymer layer is provided at about 2% w/w of the composition.

In a further alternative embodiment of the invention said composition consists essentially of about 80% w/w hydrocortisone, about 8% w/w hydroxypropylmethylcellulose and about 12% w/w ethylcellulose.

In a preferred embodiment of the invention consists of 80% w/w hydrocortisone, 8% w/w hydroxypropylmethylcellulose and 12% w/w ethylcellulose.

In a preferred embodiment of the invention hydroxyproplymethylcellulose is provided at between 0.25-0.35% w/w of the composition. Preferably, ethylcellulose is provided at between 1-2% w/w.

In preferred embodiment of the invention hydroxyproplymethylcellulose is provided at about 0.3% w/w and ethylcellulose is provided at about 1.2% w/w of the composition.

In a preferred embodiment of the invention said composition comprises:
  i) a carrier consisting essentially of at least 60% w/w micro-particulates;
  ii) a drug layer consisting essentially of at least 0.60% w/w hydrocortisone and at least 0.60% w/w hydroxyproplymethylcellulose contacting the carrier;
  iii) a sealing layer consisting essentially of at least 29% w/w hydroxyproplymethylcellulose and at least 2% magnesium stearate contacting said drug layer; and
  i) a taste masking layer consisting essentially of at least 0.25% w/w hydroxyproplymethylcellulose and at least 1% w/w ethylcellulose and at least 0.4% w/w magnesium stearate contacting said sealing layer.

Preferably, said composition is defined in table 4.

In a preferred embodiment of the invention composition is adapted for substantially immediate release of hydrocortisone.

Preferably, hydrocortisone is not substantially released before about 5 minutes in aqueous conditions in the mouth.

In a preferred embodiment of the invention hydrocortisone is released after swallowing.

Preferably the adrenal insufficiency is caused by a condition selected from the group consisting of: primary or secondary or tertiary adrenal failure, congenital adrenal hyperplasia, late-onset congenital adrenal hyperplasia, polycystic ovarian failure, Glucocorticoid-remediable aldosteronism (GRA).

In a preferred embodiment of the invention adrenal insufficiency is caused by congenital adrenal dysfunction.

Compositions suitable for oral administration may be presented as discrete units, such as capsules, tablets, mini-tablets, lozenges, each containing a predetermined amount of the active.

In a preferred embodiment of the invention said composition is a tablet or capsule; preferably a capsule.

Other compositions include suspensions in aqueous liquids or non-aqueous liquids. Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

When administered the hydrocortisone preparation is administered in pharmaceutically acceptable preparations. Such preparations may routinely contain pharmaceutically acceptable concentrations of salt, buffering agents, preservatives and compatible carriers.

Such amounts will depend, of course, on the particular condition being treated, the severity of the condition, the individual patient parameters including age, physical condition, size and weight, the duration of the treatment, the nature of concurrent therapy (if any), and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

The hydrocortisone preparation used contains an effective amount of drug for producing the desired response in a unit of weight or volume suitable for administration to a patient.

The doses of hydrocortisone administered to a subject can be chosen in accordance with different parameters, in particular the state of the subject, their body surface area, and also their weight. Other factors include the desired period of treatment. In the event that a response in a subject is insufficient at the initial doses applied, higher doses (or effectively higher doses by a different, more localized delivery route) may be employed to the extent that patient tolerance permits.

Administration of hydrocortisone preparations to mammals other than humans, (e.g. for testing purposes or veterinary therapeutic purposes), is carried out under substantially the same conditions as described above although dosages will vary in accordance with the size of the animal treated. Steroid treatment is used in animals both for any cause of adrenal insufficiency but in addition for any cause of inflammation, joint disease, and cancer. A subject, as used herein, is a mammal, preferably a human, and including a non-human primate, cow, horse, pig, sheep, goat, dog, cat or rodent.

When administered, the hydrocortisone preparation is administered in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Hydrocortisone preparations may be combined, if desired, with a pharmaceutically-acceptable carrier. The term "pharmaceutically-acceptable carrier" as used herein means one or more compatible solid or liquid fillers, diluents or encapsulating substances which are suitable for administration into a human and are typically inert. The term "carrier" denotes an organic or inorganic ingredient, natural or synthetic, with which the active ingredient is combined to facilitate the application. The components of the pharmaceutical compositions also are capable of being co-mingled with hydrocortisone, and with each other, in a manner such that there is no interaction which would substantially impair the desired pharmaceutical efficacy.

The multiparticulate core matrix is combined with pharmaceutically acceptable excipients, which may include: (a) fillers such as lactose, manitose, dicalcium phosphate, microcrystalline cellulose, starch, pre-gelatanised starch, (b) binders such as hydroxypropylmethyl cellulose, polyvinyl pyrrolidone, polyvinyl acetate, (c) powder flow enhancers such colloidal silicon dioxide (d) lubricants such as magnesium stearate, sodium stearyl fumarate (e) disintegrants such as sodium starch glycollate and polyvinyl pyrrolidone and (f) anti-sticking agents such as talc (g) taste masking agents such as sucrose, cellulose acetate, cellulose butyrate, polyvinyl acetate, polyvinyl alcohol, polymetharylates.

According to a further aspect of the invention there is provided a pharmaceutical composition consisting essentially of 80-90% w/w hydrocortisone, 9-16% w/w cellulose acetate and 1-4% polyvinyl pyrrolidone.

In a preferred embodiment of the invention said composition consists of 80% w/w hydrocortisone, 16% w/w cellulose acetate and 4% polyvinyl pyrrolidone.

According to a further aspect of the invention there is provided a pharmaceutical composition consisting essentially of 60-80% w/w hydrocortisone, 5-10% w/w aminoalkyl methacrylate and 10-35% w/w polyvinyl acetate.

In a preferred embodiment of the invention said composition consists of 80% w/w hydrocortisone, 10% w/w aminoalkyl methacrylate and 10% polyvinyl acetate.

In a preferred embodiment of the invention said composition consists of 60% w/w hydrocortisone, 10% w/w aminoalkyl methacrylate and 30% w/w polyvinyl acetate.

In a preferred embodiment of the invention said composition consists of 60% w/w hydrocortisone, 5% w/w aminoalkyl methacrylate and 35% w/w polyvinyl acetate.

According to a further aspect of the invention there is provided a pharmaceutical composition consisting essentially of about 80% w/w hydrocortisone, about 8% w/w hydroxypropylmethylcellulose and about 12% w/w ethylcellulose.

In a preferred embodiment of the invention consists of 80% w/w hydrocortisone, 8% w/w hydroxypropylmethylcellulose and 12% w/w ethylcellulose.

According to a further aspect of the invention there is provided a treatment regimen for the control of adrenal insufficiency in a subject comprising: administering an effective amount of a composition according to the invention to a subject in need of treatment for adrenal insufficiency at least once a day.

In a preferred method of the invention said composition is administered three to four times a day at approximately six hour intervals.

In a preferred method of the invention said subject is a paediatric, elderly or non-human animal subject.

According to an aspect of the invention there is provided a process for the manufacture of a hydrocortisone pharmaceutical formulation comprising the steps:
i) forming a solution comprising hydrocortisone and a binding agent;
ii) providing a micro-particulate carrier;
iii) apply the hydrocortisone solution to the micro-particulate carrier to coat said carrier;
iv) dry the hydrocortisone coated micro-particulate carrier;
v) forming a solution comprising a sealing polymer and applying the sealing polymer solution to the dried micro-particulate carrier; and
vi) forming a solution comprising a taste masking polymer and applying the taste masking polymer to the sealed hydrocortisone coated micro-particulate carrier to form a layered hydrocortisone pharmaceutical formulation.

In a preferred method of the invention the binding agent includes hydroxyproplymethylcellulose.

In a preferred method of the invention the micro-particulate carrier is micro-crystalline cellulose or sugar beads.

In a preferred method of the invention the sealing polymer includes hydroxyproplymethylcellulose.

In a preferred method of the invention the taste masking polymer includes hydroxyproplymethylcellulose.

In a preferred method of the invention the taste masking polymer further includes ethycellulose.

Preferably, the hydrocortisone and the binding agent solution, the sealing polymer solution and the taste masking polymer solution are applied as a spray.

According to a further aspect of the invention there is provided a pharmaceutical formulation manufactured by a process according to the invention.

According to a further aspect of the invention there is provided a pharmaceutical composition comprising:
i) a carrier consisting essentially of at least 60% w/w micro-particulates;
ii) a drug layer consisting essentially of at least 0.60% w/w hydrocortisone and at least 0.60% w/w hydroxyproplymethylcellulose contacting the carrier;
iii) a sealing layer consisting essentially of at least 29% w/w hydroxyproplymethylcellulose and at least 2% magnesium stearate contacting said drug layer; and
ii) a taste masking layer consisting essentially of at least 0.25% w/w hydroxyproplymethylcellulose and at least 1% w/w ethylcellulose and at least 0.4% w/w magnesium stearate contacting said sealing layer.

Preferably, said composition is defined in table 4.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figure:

FIGURE: Dissolution profile: Formulation D: Dissolution was undertaken using United States Pharmacopeial, Method 2 (paddle) in 900 ml phosphate buffer at agitation speed 100 rpm. Data shown is mean of n=3.

An embodiment of the invention will now be described by example only and with reference to the following materials, methods and tables:

Materials And Methods
Definitions

"Binding agent": is a substance used to cause adhesion of powder particles in tablet granulations such as: Alginic acid, carboxymethylcellulose, sodium compressible sugar, ethylcellulose gelatin, liquid glucose, methylcellulose, povidone, pregelatinized starch.

"Micro-particulate carrier": is defined as a particulate dispersions or solid particles with a size in the range of 1-1000 μm on which the desired drug is dissolved, entrapped, encapsulated or attached to a microparticle matrix.

"Sealing polymer coat": provides a moisture barrier and a hard tablet surface to prevent attritional effects. Coating materials include sugar, waxes, shellac, cellulose derivatives, gelatin, organic acids, aminoalkyl aryl polymers or polyvinylstyrene compounds.

"Immediate release": a dosage form that is intended to release the active ingredient(s) on administration or after a short delay with no enhanced, delayed or extended release effect.

Dissolution Methodology

Dissolution testing of Hydrocortisone Immediate Release multi-particulates was conducted using USP Apparatus I (Baskets), with a total of 900 mL of dissolution media (pH1.2).

Assay of Hydrocortisone

The concentration of Hydrocortisone in the multi-particulates and released during the dissolution evaluation was determined using the following method. The hydrocortisone solution was diluted in the mobile phase solution comprising tetrahydrofuran/water (20:80 v/v). The resulting solution was into a HPLC, set-up with a Phenomenex Luna column C18(2), 5 μm, 150 mm×4.6 mm, equilibrated at 45° C. The samples were run using Isocratic conditions employing tetrahydrofuran/water (20:80 v/v) as the mobile phase at a flow rate of 1.5 mL/minute. Detection is by UV at a wavelength of 254 nm.

Dosage Regimen for Paediatric Patients

In infants HC is usually administered in a dose of 12 to 18 mg/m2 body surface area per day. In the early phase of treatment, infants may require up to 25 mg/m2/day of hydrocortisone to reduce markedly elevated adrenal hormones. This dose range exceeds the daily cortisol secretory rate of normal infants and children, which is estimated to be 7 to 9 mg/m2 body surface area in neonates and 6 to 7 mg/m2 body surface area in children and adolescents. The treatment is usually split into three or four doses. In a premature infant you might use 0.25 mg four times daily given six hourly. In a normal sized neonate you would be looking at 0.5 mg to 1.0 mg thrice or four times daily (6 hourly). For children dosing would be between 1.0 to 2.0 mg three times daily with the first dose given on waking the second at midday and the third in the evening. A larger dose usually being given in the morning. The same is true for adolescents but the total daily dose would be increased according to body surface area to between 5 to 20 mg.

In the dosing regimen would be best given thrice daily as illustrated in table below:

| Patient Weight (kg) | Total Hydrocortisone Dose per day (mg) | First Morning Hydrocortisone Dose (mg) | Second Midday Hydrocortisone Dose (mg) | Third Evening Hydrocortisone Dose (mg) |
|---|---|---|---|---|
| 50-54 | 10.0 | 5.0 | 2.5 | 2.5 |
| 55-74 | 15.0 | 7.5 | 5.0 | 2.5 |
| 75-84 | 17.5 | 10.0 | 7.5 | 2.5 |
| 85-94 | 20.0 | 10.0 | 7.5 | 2.5 |
| 95-114 | 22.5 | 12.5 | 7.5 | 2.5 |
| 115-120 | 25.0 | 15.0 | 7.5 | 2.5 |

Formulations Used in Paediatric Dosage Regimen
Formulation 1a (Water-Insoluble Polymer Example)

| Component | mg | % w/w |
|---|---|---|
| Hydrocortisone micronized EP USP | 5.00 | 80.0 |
| Cellulose acetate | 1.00 | 16.0 |
| Polyvinyl pyrrolidone | 0.25 | 4.0 |
| Total | 6.25 | 100.0 |

Formulation 1b (Water-Insoluble Polymer Example)

| Component | mg | % w/w |
|---|---|---|
| Hydrocortisone micronized EP USP | 1.00 | 90.0 |
| Cellulose acetate | 0.10 | 9.0 |
| Polyvinyl pyrrolidone | 0.01 | 1.0 |
| Total | 1.11 | 100.0 |

Method of Preparation

1) The hydrocortisone is fluidized in a fluid bed mixer (Glatt GPC-G3) at 25'C
2) The polymer solution is formed by mixing cellulose acetate with polylyvinyl pyrrolidone in an acetone/water mixture (9:1 volume ratio) to form a solution with polymer content of 6.7%
3) The polymer solution is sprayed onto the fluidized hydrocortisone in the fluid bed mixer (Glatt GPC-G3) at 25'C using the following process parameters: atomising air pressure (1.5-2.0 bar), inlet air volume 60 cm$^3$/sec. The weight gain is adjusted based on the formula requirements
4) The polymer coat is allowed to cure for 10-20 minutes in the fluid bed mixer (Glatt GPC-G3) prior to discharge 5) The final product is filled into the appropriate dispensing vehicle/device Formulation 2a (Reverse Enteric Polymer Blends)

| Component | mg | % w/w |
|---|---|---|
| Hydrocortisone micronized EP USP | 5.00 | 80.0 |
| Aminoalkyl methacrylate copolymer | 0.63 | 10.0 |
| Polyvinyl acetate | 0.63 | 10.0 |
| Total | 6.26 | 100.0 |

Formulation 2b (Reverse Enteric Polymer Blends)

| Component | mg | % w/w |
|---|---|---|
| Hydrocortisone micronized EP USP | 5.00 | 60.0 |
| Aminoalkyl methacrylate copolymer | 0.83 | 10.0 |
| Polyvinyl acetate | 2.50 | 30.0 |
| Total | 8.33 | 100.0 |

Formulation 2c (Reverse Enteric Polymer Blends)

| Component | mg | % w/w |
|---|---|---|
| Hydrocortisone micronized EP USP | 1.00 | 60.0 |
| Aminoalkyl methacrylate copolymer | 0.08 | 5.0 |
| Polyvinyl acetate | 0.58 | 35.0 |
| Total | 1.66 | 100.0 |

Method of Preparation
1) The hydrocortisone is fluidized in a fluid bed mixer (Glatt GPC-G3) at 25'C
2) The polymer solution is formed by mixing Aminoalkyl methacrylate copolymer with Polyvinyl acetate in an acetone/isopropanol/water mixture (4:4:1 volume ratio) to form a solution with polymer content of 6.7%
3) The polymer solution is sprayed onto the fluidized hydrocortisone in the fluid bed mixer (Glatt GPC-G3) at 25'C using the following process parameters: atomising air pressure (1.5-2.0 bar), inlet air volume 60 cm$^3$/sec. The weight gain is adjusted based on the formula requirements
4) The polymer coat is allowed to cure for 10-20 minutes in the fluid bed mixer (Glatt GPC-G3) prior to discharge
5) The final product is filled into the appropriate dispensing vehicle/device Formulation 3a (Hydrophilic Swellable Polymer)

| Component | mg | % w/w |
|---|---|---|
| Hydrocortisone micronized EP USP | 5.00 | 80.0 |
| hydroxypropylmethycellulose | 0.50 | 8.0 |
| Ethylcellulose | 0.75 | 12.0 |
| Total | 6.25 | 100.0 |

Method of Preparation
1) The hydrocortisone is fluidized in a fluid bed mixer (Glatt GPC-G3) at 25'C
2) The polymer solution is formed by mixing hydroxypropylmethylcellulose with Ethylcellulose (Surelease) in water to form a solution with polymer content of 8.0%
3) The polymer solution is sprayed onto the fluidized hydrocortisone in the fluid bed mixer (Glatt GPC-G3) at 40'C using the following process parameters: atomising air pressure (1.5-2.0 bar), inlet air volume 60 cm$^3$/sec. The weight gain is adjusted based on the formula requirements
4) The polymer coat is allowed to cure for 30 minutes in the fluid bed mixer (Glatt GPC-G3) prior to discharge
5) The final product is filled into the appropriate dispensing vehicle/device.

Formulation Used in Paediatric Dosage Regimen
Formulation D Description:
Inert Cellets® 350 core coated with a drug-layer, comprising hydrocortisone and hydroxypropylmethyl cellulose (HPMC, Pharmacoat 606), a seal coat encasing the drug-layer comprising HMPC (Pharmacoat 606) and magnesium stearate, and an outer taste-masking layer, comprising HPMC (Pharmacoat 603), ethyl cellulose (Ethocel std 10) and magnesium stearate.

The qualitative and quantitative composition of formulation D is shown in Table 1.

TABLE 4

Qualitative and quantitative composition of Formulation D at the dose strengths 0.5 mg, 1.0 mg, 2.0 mg and 5.0 mg

| | Function | Quantity per dosage (mg) | | | | Quantity per dosage (%) |
|---|---|---|---|---|---|---|
| Inert core | | | | | | |
| Cellets ® 350 | Inert carrier | 49.28 | 98.55 | 197.12 | 492.75 | 64.06 |
| Drug-layer | | | | | | |
| Hydrocortisone[1] | Active | 0.50 | 1.00 | 2.00 | 5.00 | 0.65 |
| Hydroxypropylmethyl cellulose (HMPC)[2] | Binder | 0.50 | 1.00 | 2.00 | 5.00 | 0.65 |
| Purified water(*) | | 20.00 | 40.00 | 80.00 | 200.00 | — |
| Seal coat | | | | | | |
| Hydroxypropylmethyl cellulose (HMPC)[2] | Sealant coat | 22.86 | 45.71 | 91.44 | 228.55 | 29.71 |
| Magnesium stearate | Anti-sticking agent | 2.29 | 4.57 | 9.16 | 22.85 | 2.97 |

TABLE 4-continued

Qualitative and quantitative composition of Formulation D at the dose strengths 0.5 mg, 1.0 mg, 2.0 mg and 5.0 mg

|  | Function | Quantity per dosage (mg) | | | | Quantity per dosage (%) |
|---|---|---|---|---|---|---|
| Purified water(*) | | 228.60 | 457.20 | 914.40 | 2286.00 | — |
| Taste-masking layer | | | | | | |
| Hydroxypropylmethyl cellulose (HMPC)[3] | Taste-masking polymer | 0.23 | 0.46 | 0.92 | 2.30 | 0.30 |
| Ethyl cellulose[4] | Taste-masking polymer | 0.93 | 1.86 | 3.72 | 9.30 | 1.21 |
| Magnesium stearate | Anti-sticking agent | 0.35 | 0.69 | 1.40 | 3.45 | 0.45 |
| Purified water(*) | Vehicle | 5.70 | 11.40 | 22.80 | 57.00 | — |
| Ethanol(*) | Vehicle | 22.80 | 45.60 | 91.20 | 228.00 | — |
| TOTAL | | 76.94 | 153.84 | 307.76 | 769.20 | 100.00 |

[1]Supplied as Hydrocortisone USP Micronized EP (Pfizer)
[2]Supplied as Pharmacoat 606 (Shin-Etsu)
[3]Supplied as Pharmacoat 603 (Shin-Etsu)
[4]Supplied as Ethocel standard 10 (Dow Chemicals)
(*)Removed during processing, not included in final formulation Manufacturing Process for Formulation D for all Dose Strengths
Description of Drug-Layering Process Step (1)
1. Weigh out the Cellets® 350, Hydrocortisone and hydroxypropyl methyl cellulose (HPMC) binder material and purified water in the relevant batch quantities
2. In an appropriate vessel prepare the drug layering suspension by adding the HPMC binder to purified water and stir with an overhead stirrer until the HMPC binder is fully dissolved
3. Add the Hydrocortisone to the binder solution and mix with a high-sheer stirrer or homogeniser to form a homogeneous suspension
4. Remove the high-sheer stirrer or homogeniser and replace with an overhead stirrer. Ensure the suspension is mixed throughout the spray process
5. Set up the fluid-bed dryer with the appropriate spray attachment and retaining basket
6. Place the Cellets® 350 into the fluid-bed dryer and fluidise until the product temperature reaches above 20° C.
7. Spray on the Hydrocortisone suspension onto the Cellets® 350
8. Determine the end-point by the amount of suspension sprayed onto the batch by weight (accounting for coating process efficiency)
9. After the spraying process has finished the Hydrocortisone coated Cellets® material is kept fluidised for 30 minutes to allow sufficient drying
10. Sieve the Hydrocortisone coated Cellets® through a 1.4 mm sieve to remove any agglomerates Description of Seal-Coat Layering Step (2)
1. Weigh out the HPMC, magnesium stearate and purified water in the relevant batch quantities
2. Dissolve the HPMC in purified water to form the seal coat solution
3. Set up the fluid-bed dryer with the appropriate spray attachment and retaining basket
4. Add the magnesium stearate to the Hydrocortisone coated Cellets® (from step 1) and apply low sheer dry blending
5. Place the magnesium stearate Hydrocortisone coated Cellets® blend into the fluid-bed dryer and fluidise until a product temperature of between 20° C. and 25° C. is reached
6. Spray on the HPMC solution to the magnesium stearate Hydrocortisone coated Cellets®
7. Determine the end-point by the amount of solution sprayed onto the batch by weight
8. Screen the coated material through a 1.4 mm sieve if appropriate to remove agglomerates Description of the Taste-Masking Step (3)
1. Weigh out the HPMC, Ethyl cellulose, purified water and ethanol in the relevant quantities
2. Mix together the HPMC, Ethyl cellulose in the purified water and ethanol mixture using an overhead stirrer until a solution is obtained
3. Set up the fluid-bed dryer with the appropriate spray attachment and retaining basket
4. Add the magnesium stearate to the seal coated Hydrocortisone coated Cellets® (from step 2) and apply low sheer dry blending
5. Place the magnesium stearate seal coated Hydrocortisone coated Cellets® into the fluid-bed dryer and fluidise until a product temperature of between 20° C. and 25° C. is reached
6. Spray on the taste-masking polymer solution to the magnesium stearate seal coated Hydrocortisone coated Cellets®
7. Determine the end-point by the amount of solution sprayed onto the batch by weight Dissolution Profile: Formulation D
Dissolution Methodology Dissolution was undertaken using United States Pharmacopeial, Method 2 (paddle) in 900 ml simulated gastric fluid (pH 1.2) at agitation speed 100 rpm. Data shown is mean of n=3. This is illustrated in the FIGURE.

The invention claimed is:
1. A method for treating adrenal insufficiency in a human in need thereof, the method comprising:
orally administering to the human an oral dosage form comprising a plurality of hydrocortisone-containing multilayer microparticles, wherein each of the hydrocortisone-containing multilayer microparticles comprises:
(i) an inert core consisting essentially of microcrystalline cellulose;
(ii) a sealing layer consisting of hydroxypropyl methylcellulose and magnesium stearate;
(iii) an active agent layer between the inert core and the sealing layer, the active agent layer comprising hydrocortisone and hydroxypropyl methylcellulose; and
(iv) an exterior layer for taste-masking comprising hydroxypropyl methylcellulose and ethyl cellulose; and
wherein the hydrocortisone in the active agent layer constitutes about 0.65% by weight of the hydrocortisone-containing multilayer microparticle; and
wherein the plurality of hydrocortisone-containing multilayer microparticles collectively comprises a therapeutically effective amount of hydrocortisone.

2. The method of claim 1, wherein the oral dosage form is selected from the group consisting of tablet, capsule, and liquid.

3. The method of claim 1, wherein the oral dosage form is a suspension.

4. The method of claim 1, wherein the oral dosage form is a foodstuff or a drink.

5. The method of claim 1, wherein the oral dosage form is an immediate-release dosage form.

6. The method of claim 1, wherein the human is a pediatric subject.

7. The method of claim 1, wherein the human is an elderly subject.

8. The method of claim 1, wherein the adrenal insufficiency is selected from the group consisting of primary or secondary or tertiary adrenal failure, congenital adrenal hyperplasia, late-onset congenital adrenal hyperplasia, polycystic ovarian failure, and glucocorticoid-remediable aldosteronism (GRA).

9. The method of claim 1, wherein the adrenal insufficiency is congenital adrenal dysfunction.

10. The method of claim 1, wherein the hydrocortisone-containing multilayer microparticles have a diameter between 100 µm-1200 µm.

11. The method of claim 1, wherein the hydrocortisone-containing multilayer microparticles have a diameter between 400 µm-1000 µm.

12. The method of claim 1, wherein the hydroxypropyl methylcellulose in the active agent layer constitutes between 0.60-0.70% by weight of the hydrocortisone-containing multilayer microparticle.

13. The method of claim 1, wherein the hydroxypropyl methylcellulose in the active agent layer constitutes about 0.65% by weight of the hydrocortisone-containing multilayer microparticle.

14. The method of claim 1, wherein the therapeutically effective amount of hydrocortisone is between 0.25 mg and 30 mg.

15. The method of claim 1, wherein the therapeutically effective amount of hydrocortisone is selected from the group consisting of about 0.25 mg, about 0.5 mg, about 1.0 mg, about 2.0 mg, about 5.0 mg, about 10 mg, about 20 mg, and about 30 mg.

16. The method of claim 1, wherein the sealing layer constitutes 25-35% by weight of the hydrocortisone-containing multilayer microparticle.

17. The method of claim 1, wherein the sealing layer constitutes about 30% by weight of the hydrocortisone-containing multilayer microparticle.

18. The method of claim 1, wherein the exterior layer for taste-masking constitutes between 0.5 and 2.5% by weight of the hydrocortisone-containing multilayer microparticle.

19. The method of claim 1, wherein the exterior layer for taste-masking constitutes about 2% by weight of the hydrocortisone-containing multilayer microparticle.

20. The method of claim 1, wherein the exterior layer for taste-masking further comprises magnesium stearate.

21. The method of claim 1, wherein the hydroxypropyl methylcellulose in the exterior layer for taste-masking constitutes between 0.25%-0.35% by weight of the hydrocortisone-containing multilayer microparticle.

22. The method of claim 1, wherein the ethylcellulose in the exterior layer for taste-masking constitutes between 1%-2% by weight of the hydrocortisone-containing multilayer microparticle.

23. The method of claim 1, wherein (1) the hydroxypropyl methylcellulose in the exterior layer for taste-masking constitutes about 0.3% by weight of the hydrocortisone-containing multilayer microparticle; and (2) the ethylcellulose in the exterior layer for taste-masking constitutes about 1.2% by weight of the hydrocortisone-containing multilayer microparticle.

24. A method for treating adrenal insufficiency in a human in need thereof, the method comprising:
orally administering to the human an effective amount of a pharmaceutical composition comprising:
i) a microcrystalline cellulose carrier coated with a drug layer, wherein microcrystalline cellulose of the microcrystalline cellulose carrier constitutes at least 60% by weight of the pharmaceutical composition;
ii) the drug layer comprises hydrocortisone and a binding agent comprising hydroxypropylmethylcellulose, wherein the hydrocortisone in the drug layer constitutes at least 0.60% by weight of the pharmaceutical composition and the hydroxypropylmethylcellulose in the drug layer constitutes at least 0.60% by weight of the pharmaceutical composition, thereby generating a hydrocortisone and hydroxypropylmethylcellulose coated microcrystalline carrier;
iii) a sealing layer comprising hydroxypropylmethylcellulose and magnesium stearate, wherein the hydroxypropylmethylcellulose in the sealing layer constitutes at least 20% by weight of the pharmaceutical composition, and the magnesium stearate in the sealing layer constitutes at least 2% by weight of the pharmaceutical composition, wherein the sealing layer contacts said hydrocortisone and hydroxypropylmethylcellulose coated microcrystalline carrier; and
iv) a taste masking polymer layer comprising hydroxypropylmethylcellulose, ethylcellulose, and magnesium stearate, wherein the hydroxypropylmethylcellulose in the taste masking polymer layer constitutes at least 0.25% by weight of the pharmaceutical composition, wherein the ethylcellulose in the taste masking polymer layer constitutes at least 1% by weight of the pharmaceutical composition, and wherein the magnesium stearate in the taste masking polymer layer constitutes at least 0.4% by weight of the pharmaceutical composition, wherein the taste masking polymer layer contacts said sealing layer, thereby forming a layered particle.

25. The method of claim 24, where the human is a pediatric subject.

26. The method of claim 24, where the human is an elderly subject.

\* \* \* \* \*